(12) United States Patent
Lowe et al.

(10) Patent No.: US 7,476,236 B2
(45) Date of Patent: Jan. 13, 2009

(54) EMBOLIC PROTECTION FILTER DELIVERY SHEATH

(75) Inventors: Brian J. Lowe, Zimmerman, MN (US); Robert L. Cassell, Otsego, MN (US); Andrew Forsberg, Minneapolis, MN (US); Colin P. Hart, Queensbury, NY (US); Thomas Deyette, Jr., Hudson Falls, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 771 days.

(21) Appl. No.: 10/738,589

(22) Filed: Dec. 16, 2003

(65) Prior Publication Data

US 2004/0158277 A1 Aug. 12, 2004

(51) Int. Cl.
*A61M 29/00* (2006.01)
(52) U.S. Cl. .................................................. 606/200
(58) Field of Classification Search ................ 606/200, 606/108, 1, 113, 114, 159; 604/93, 19, 500
See application file for complete search history.

(56) References Cited

U.S. PATENT DOCUMENTS

| | | | |
|---|---|---|---|
| 3,472,230 A | 10/1969 | Fogarty | |
| 3,570,485 A | 3/1971 | Reilly | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |
| 4,997,424 A | 3/1991 | Little | |
| 4,998,539 A | 3/1991 | Delsanti | |

(Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).
"Endovascular Grafts, Stents Drive Interventional Radiology Growth," *Cardiovascular* Device Update, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).

(Continued)

*Primary Examiner*—Kevin T Truong
(74) *Attorney, Agent, or Firm*—Crompton, Seager & Tufte LLC

(57) ABSTRACT

Embolic protection sheath and method of using the same. In some embodiments, the present invention includes an elongate shaft, an embolic protection filter coupled to the shaft, and a sheath disposed over at least a portion of the shaft.

4 Claims, 1 Drawing Sheet

U.S. PATENT DOCUMENTS

| | | |
|---|---|---|
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,322,513 A | 6/1994 | Walker |
| 5,329,942 A | 7/1994 | Gunther et al. |
| 5,330,484 A | 7/1994 | Gunther |
| 5,354,310 A | 10/1994 | Garnic et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,687,727 A | 11/1997 | Kraus et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,074,377 A * | 6/2000 | Sanfilippo, II ............... 604/500 |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,251,119 B1 | 6/2001 | Addis |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,391,044 B1 | 5/2002 | Yadav et al. |
| 6,497,681 B1 | 12/2002 | Brenner |
| 6,540,722 B1 | 4/2003 | Boyle et al. |
| 6,562,058 B2 | 5/2003 | Seguin et al. |
| 6,602,271 B2 | 8/2003 | Adams et al. |
| 6,602,273 B2 | 8/2003 | Marshall |
| 6,620,182 B1 | 9/2003 | Khosravi et al. |
| 6,623,506 B2 | 9/2003 | McGuckin, Jr. et al. |
| 6,652,505 B1 | 11/2003 | Tsugita |
| 6,656,203 B2 | 12/2003 | Roth et al. |
| 6,656,351 B2 | 12/2003 | Boyle |

FOREIGN PATENT DOCUMENTS

| | | |
|---|---|---|
| DE | 34 17 738 | 11/1985 |
| DE | 40 30 998 A1 | 10/1990 |
| DE | 199 36 207 A1 | 8/1999 |
| DE | 199 16 162 | 10/2000 |
| EP | 0 200 688 | 11/1986 |
| EP | 0 293 605 A1 | 12/1988 |
| EP | 0 391 544 A1 | 10/1990 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 732 087 A1 | 9/1996 |
| EP | 0 737 450 A1 | 10/1996 |

| | | |
|---|---|---|
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

Cragg, Andrew et al., "Nonsurgical Placement of Arterial Endoprosthesis: A New Technique Using Nitinol Wire," *AJR*, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," *Surgery*, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al., "Microemboli Detected by Transcranial Doppler Monitoring . . . ," *Cardiovascular Surgery*, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patency of Ductus Arteriosus After Balloon Dilation: an Experimental Study," Laboratory Investigation, 69(4):772-774 (Apr. 1984).
Marache et al., "Percutaneous Transluminal Venous Angioplasty . . . ," *American Heart Journal*, 125(2 Pt 1):362-366 (Feb. 1993).
Mazur et al., "Directional Atherectomy with the Omnicath™: A Unique New Catheter System," *Catheterization and Cardiovascular Diagnosis*, 31:17-84 (1994).
Moussa, MD, Issaam "Stents Dont't Require Systemic Anticoagulation . . . But the Technique (and Results) Must be Optimal," Journal of Invasive Cardiol., 8(E):3E-7E, (1996).
Nakanishi et al., "Catheter Intervention to Venous System Using Expandable Metallic Stents," *Rinsho Kyobu Geka*, 14(2):English Abstract Only (Apr. 1994).
Onal et al., "Primary Stenting for Complex Atherosclerotic Plaques in Aortic and Iliac Stenoses," *Cardiovascular & Interventional Radiology*, 21(5):386-392 (1998).
Theron et al., "New Triple Coaxial Catheter System for Carotid Angioplasty with Cerebral Protection," *American Journal of Neuroradiology*, 11:869-874 (1990).
Tunick et al., "Protruding atherosclerotic plaque in the aortic arch of patients with systemic embolization: A new finding seen by transesophageal echocardiography," *American Heart Journal* 120(3):658-660 (Sep. 1990).
Waksman et al., "Distal Embolization is Common After Directional Atherectomy . . . ," *American Heart Journal*, 129(3):430-435 (1995).
Wholey, Mark H. et al., PTA and Stents in the Treatment of Extracranial Circulation, *The Journal of Invasive Cardiology*, 8(E):25E-30E (1996).

* cited by examiner

EMBOLIC PROTECTION FILTER DELIVERY SHEATH

CROSS-REFERENCES TO RELATED APPLICATIONS

This application claims the benefit of priority to co-pending U.S. patent application Ser. No. 10/085,149, filed Feb. 27, 2002 and provisional U.S. patent application Ser. No. 60/272,544, filed Mar. 1, 2001 entitled DISTAL PROTECTION FILTER DELIVERY SHEATH, the entire disclosure of which is herein incorporated by reference.

FIELD OF THE INVENTION

The present invention pertains generally to the field of embolic distal protection. More particularly, the invention pertains to embolic and distal protection filters.

BACKGROUND OF THE INVENTION

Embolic protection filters can be used to collect debris dislodged when performing a procedure in a vessel. For example, an embolic protection filter can be placed distally of a lesion in a coronary artery when performing angioplasty. The embolic protection filter is first placed distally of the lesion. An angioplasty catheter can then be advanced to the lesion. The lesion is then dilated. Debris dislodged by the dilation of the lesion can be captured by a filter. After dilatation of the lesion, the angioplasty catheter is removed as well as the filter containing the debris.

SUMMARY OF THE INVENTION

The present invention pertains to an embolic protection filter delivery sheath assembly. The present invention include an elongate sheath, an elongate shaft (e.g., a guidewire or filter wire) adapted for being disposed with in the sheath, a filter coupled to the shaft, and a manifold coupled to the sheath. In some embodiments, the manifold including a sheath cutting blade. The sheath cutting blade can be used to split the sheath longitudinally, so that the sheath can be peeled away from the filter wire. In some embodiments, the sheath may include a slit that can allow the sheath to be spit whether the cutting blade is present or absent.

DETAILED DESCRIPTION

Figure 1:
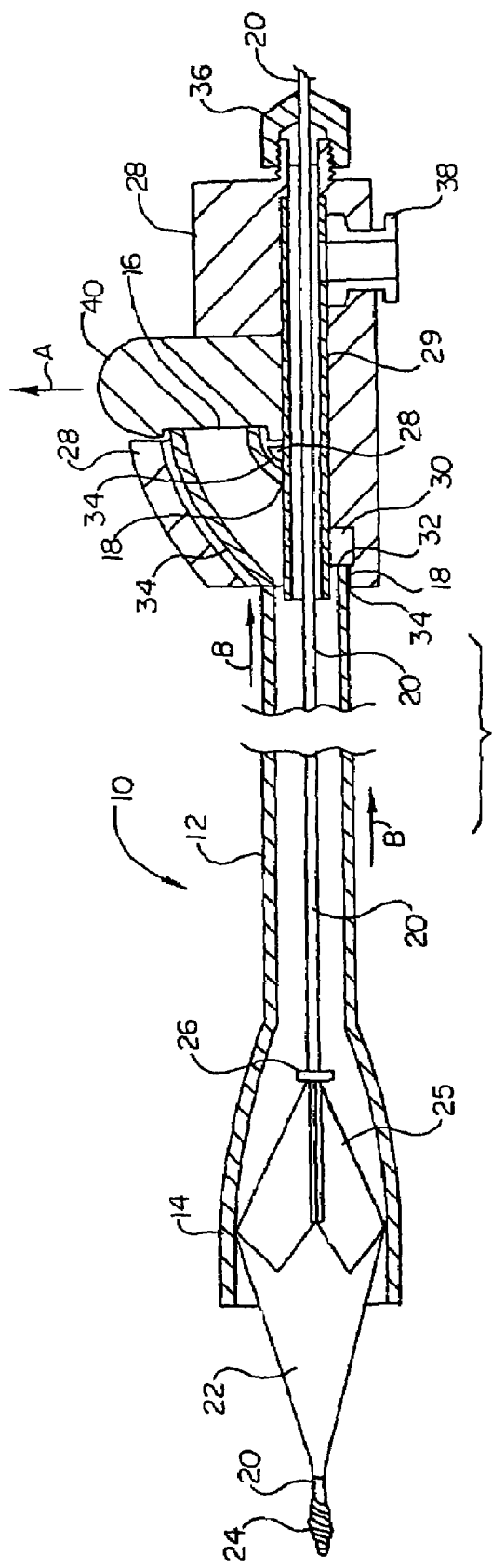
FIG. 1 is a cross-sectional view of an embodiment of an embolic protection filter delivery sheath assembly in accordance with the present invention.

The following description should be read with reference to the drawings wherein like reference numerals indicate like elements throughout the several views. The detailed description and drawings illustrate example embodiments of the claimed invention.

FIG. 1 is a cross-sectional view of an embolic protection filter delivery sheath assembly 10 in accordance with the present invention. Assembly 10 includes a tubular sheath 12 having a generally cylindrical larger diameter portion 14 and a proximal end 16. Sheath 12 may also include an opening 18 through a side wall near proximal end 16. An elongate shaft or wire 20 having an embolic protection filter coupled thereto can be slidably disposed within sheath 12.

It can be appreciated that sheath 12 is generally tubular and may comprise a number of different medical devices such as a catheter (e.g., a guide, diagnostic, or therapeutic catheter). Sheath 12 may be comprised of a polymer. For example, sheath 12 may be comprised of polyethylene (PE), polypropylene (PP), polyvinylchloride (PVC), polyether block amide (PEBA), or other suitable materials. Alternatively, sheath 12 may be comprised of a metal, metal alloy, or metal-polymer composite. In general, sheath 12 is comprised of materials having an appropriate amount of flexibility, torquability, and pushability to allow sheath 12 to be advanced through a blood vessel or other body lumen.

Wire 20 may comprise a guidewire, filter wire, or other suitable device. Wire 20 is generally metallic and may be comprised of, for example, stainless steel, nickel-titanium alloy, or other suitable materials. In embodiments where wire 20 is a guidewire, wire 20 may includes a distal tip 24, for example including a coil or spring. In some embodiments, a stop 26 is disposed on wire 20 proximally of filter 22.

Filter 22 may be comprised of a polyurethane sheet disposed over a filter frame. The polyurethane sheet has at least one opening that may be, for example, formed by known laser techniques. The holes or openings are sized to allow blood flow therethrough but restrict flow of debris or emboli floating in the body lumen or cavity. In some embodiments, the filter frame may include one or more struts 25 extending between filter 22 and wire 20.

Filter 22 is adapted to shift between a first generally closed collapsed configuration and a second generally expanded configuration for collecting debris in a body lumen. In some embodiments, filter 22 is biased to be in the expanded configuration. Thus, filter 22 can be at least partially collapsed within sheath 12 and may "self-expand" when sheath 12 is withdrawn from filter 22.

Embolic protection filter delivery sheath assembly 10 includes a manifold housing 28 located at proximal end 16 of sheath 12. Manifold housing 28 is available to the clinician for manipulating or otherwise actuating or holding assembly 10. It can be appreciated that modifications to the general shape or material composition of manifold housing 28 can be substituted without departing from the spirit of the invention.

A hypotube 29 can be affixed to and/or disposed within manifold housing 28 (and/or within a lumen defined by housing 28). Hypotube 29 may serve as a conduit for wire 20 to pass through or otherwise separate from sheath 12. Separation of sheath 12 and wire 20 may be important because sheath 12 may need to be moved relative to wire 20. Moving sheath 12 in the proximal direction relative to wire 20 may allow filter 22 to shift from the collapsed configuration to the expanded configuration.

A blade 30 can be affixed to or within housing 28. Blade 30 may include a distally disposed cutting edge 32. Blade 30 is configured to cut or otherwise split sheath 12. In some embodiments, sheath 12 can be cut by pulling sheath 12 across blade 30 and/or cutting edge 32.

A proximal portion of sheath 12 is disposed within an opening 34 defined by manifold housing 28. Opening 34 may define a position where sheath 12 and wire 20 are separated by manifold housing 28. A opening 34, sheath 12 may curve or bend laterally (i.e., away from the longitudinal axis along the majority of the length of sheath 12). Wire 20 generally continues in the direction of the longitudinal axis. A portion of filter wire 20 can extend longitudinally through hypotube 29 and can be held in place relative to manifold 28 (and, thus, sheath 12) by a collet 36 threadably connected to housing 28. Housing 28 also includes a lure fitting 38 for prepping sheath 10.

A pull tab 40 is releasably connected to housing 28. Distal end 16 of sheath 12 is connected to pull tab 40 by adhesive or another method. Pull tab 40 and sheath 12 are connected at or near the portion of sheath 14 that curves laterally away from the longitudinal axis. Pull tab 40 may, for example, comprise a thumb ring, finger ring, or other graspable surface that can be pulled away from manifold housing 28. Because sheath 12 is connected to pull tab 40, pull tab 40 may be used to move sheath 12. Sheath 12 may be split, cut, opened, etc. by using pull tab 40 to pull sheath 12 across blade 30. In embodiments where sheath 12 includes a slit, actuating pull tab 40 may allow sheath 12 to become spit along the slit.

Embolic protection filter delivery sheath 10 can be used in conjunction with filter 22 to provide embolic protection from embolism during procedures performed in a patient's vasculature. For example, filter 22 can be delivered distally of a coronary lesion using assembly 10. Prior to delivery, filter 22 is positioned in sheath 12 as shown. Collet 36 is tightened to fix the position of filter 22 relative to manifold 28 (and sheath 12). Saline is introduced through lure fitting 38 and hypotube 29 to flush air from sheath 12 and distal larger diameter portion 14. When filter 22 is positioned as shown in FIG. 1, sheath 12 and filter 22 can be advanced through a blood vessel or body lumen to a location distal of the lesion to be treated.

Once sheath 10 and filter 22 are advanced distally of the lesion, sheath 12 is "peeled away", generally moved proximally, and/or removed from the blood vessel to deploy filter 22. In some embodiments, sheath 12 is completed removed from assembly 10 (and, thus, the blood vessel). When sheath 12 is removed, an angioplasty catheter (or any other suitable guide, diagnostic, or therapeutic catheter) can be advanced over filter wire 20 to the lesion. The lesion may then be dilated by the angioplasty catheter. The angioplasty catheter and filter assembly 10 may then removed.

To remove sheath 10 from filter wire 20 and filter 22, pull tab 40 is pulled from manifold 28 generally in the direction of arrow A. This will draw sheath 12 proximally as shown by arrows B. As sheath 12 moves in the direction of arrows B, sheath 12 is sliced longitudinally by cutting edge 32 of blade 30. Thus, an elongate slit will extend from side opening 18 and distal larger diameter portion 14 will move proximally until it becomes disposed proximate manifold 28. In some embodiments, collet 36 is loosened and manifold 28 and larger diameter portion 14 may be removed proximally from filter wire 20. Alternatively, pull tab 40 may be actuated until the entire length of sheath 12 is sliced open and can be removed from assembly 10 and/or the blood vessel.

It can be appreciated that a slit can be pre-formed in sheath 12 such that blade 32 would not be necessary. Alternately, a narrow longitudinal region of sheath 12 could be thinned to peel away sheath 12 from wire 20 without the need of blade 30.

By peeling or otherwise removing sheath 12 at least in part away from wire 20 rather than removing it entirely over the proximal end wire 20, a shorter filter wire 20 can be used. Thus, if sheath 12 is split along a sufficient amount of its length, wire 20 can be short enough to enable single operator removal of sheath 12.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An apparatus for delivering an intravascular filter, comprising:
    an elongate sheath having a proximal end, a flared distal end, a longitudinal axis, and a lumen extending through the distal end of the elongate sheath;
    an elongate shaft having a proximal end and a distal end, the shaft disposed within the lumen of the sheath;
    a preformed slit formed along at least a portion of the longitudinal axis of the sheath;
    a filter coupled to the distal end of the shaft; and
    a handle coupled to the proximal end of the sheath, the handle including a pull tab attached to the sheath, the pull tab including a thumb ring, or a finger ring, wherein actuating the pull tab causes the sheath to split open along the preformed slit.

2. The apparatus of claim 1, further comprising a manifold in abutting relationship to the handle, the elongate shaft and the sheath at least partially disposed within the manifold.

3. The apparatus of claim 2, wherein the handle has a proximally facing surface in contact with the manifold.

4. The apparatus of claim 3, wherein the handle is coupled to the sheath at a distal region of the handle.

* * * * *